United States Patent
Jacobson

Patent Number: 5,097,067
Date of Patent: Mar. 17, 1992

[54] CARBOXY ACIDS DERIVED FROM HETEROATOM CONTAINING 3,3-BIS-PERFLUOROALKYL OXETANES

[75] Inventor: Michael Jacobson, Haworth, N.J.

[73] Assignee: Ciba-Geigy Corporation, Ardsley, N.Y.

[21] Appl. No.: 620,232

[22] Filed: Nov. 29, 1990

Related U.S. Application Data

[63] Continuation-in-part of Ser. No. 444,073, Nov. 30, 1989.

[51] Int. Cl.$^5$ .................. C07C 59/235; C07C 59/295
[52] U.S. Cl. .................................... 562/582; 549/511; 562/581; 562/583
[58] Field of Search .................... 562/582, 583, 581

[56] References Cited

U.S. PATENT DOCUMENTS

| | | | |
|---|---|---|---|
| 2,915,554 | 12/1959 | Ahlbrecht et al. | 564/96 |
| 2,965,659 | 12/1960 | Tiers | 260/408 |
| 3,088,849 | 5/1963 | Friedlander | 428/422 |
| 3,544,663 | 12/1970 | Hamptschelm et al. | 525/200 |
| 3,655,732 | 4/1972 | Roodestvedt, Jr. | 560/222 |
| 3,838,165 | 9/1974 | Blochl | 548/320 |
| 4,113,772 | 9/1978 | Lagon et al. | 562/583 |
| 4,584,143 | 4/1986 | Falk | 558/240 |
| 4,760,198 | 7/1988 | Bierschenk et al. | 562/583 |
| 4,898,981 | 2/1990 | Falk et al. | 568/28 |

FOREIGN PATENT DOCUMENTS

| | | | |
|---|---|---|---|
| 2109966 | 9/1972 | Fed. Rep. of Germany. | |
| 2116105 | 9/1972 | Fed. Rep. of Germany. | |
| 0099552 | 6/1982 | Japan | 562/583 |

OTHER PUBLICATIONS

C. Krespan, J. Org. Chem., 43 4, (1978).
Chem. Abst. 88, 61965g (1978).
Chem. Abst. 68, 115832u (1968).
Chem. Abst. 87, 68358z (1977).

Primary Examiner—C. Warren Ivy
Assistant Examiner—Amelia A. Owens
Attorney, Agent, or Firm—Luther A. R. Hall

[57] ABSTRACT

Heteroatom containing $R_f$-neopentyl compounds having formula III or IV

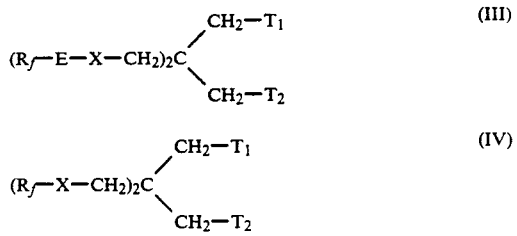

wherein $R_f$ is a straight chain perfluoroalkyl of 1 to 18 carbon atoms, E is branched or straight chain alkylene of 2 to 10 carbon atoms or said alkylene interrupted by one to three groups selected from the group consisting of —NR—, —S—, —COO—, —OOC—, $SO_2$—, —CONR—, —NRCO—, —$SO_2$NR—, and —NR$SO_2$—, or terminated at the $R_f$ end with —CONR— or —$SO_2$NR—, where $R_f$ is attached to the carbon or sulfur atom, or $R_f$ is trifluoroethylene, and for formula III, X is —S—, —$SO_2$—, or —NR—, or for formula IV, X is —CONR—, or —$SO_2$NR—, or a direct bond where $R_f$ is attached to the carbon or sulfur atom, and where R is independently hydrogen, alkyl of 1 to 6 carbon atoms or hydroxyalkyl of 2 to 6 carbon atoms, and one or both of $T_1$ and $T_2$ is the residue of a mercapto mono- or dicarboxylic acid of 2 to 4 carbon atoms after removal of the hydrogen from the mercapto group and the other of $T_1$ and $T_2$ is hydroxyl.

1 Claim, No Drawings

CARBOXY ACIDS DERIVED FROM HETEROATOM CONTAINING 3,3-BIS-PERFLUOROALKYL OXETANES

This is a continuation-in-part of Ser. No. 7/444,073 filed Nov. 30, 1989 now pending.

BACKGROUND OF THE INVENTION

This invention relates to hetero group containing perfluoroalkyl terminated oxetanes, their reaction products with nucleophiles, related halogenated derivatives, and derived polyethers. Their primary use is to impart oil and water repellency to textiles, glass, paper, leather, and other compositions.

Oxetanes connected by sulfur atoms to bis-perfluoroalkyl substituents have not been reported. Oxetanes connected by oxygen atoms to branched perfluoroalkyl groups or to fluoroalkyl groups with terminal hydrogen atoms have been described by C. Krespan in J. Org. Chem. 43, 4 (1978), Ger. Offen. 2,109,966 and 2,116,105, and by Vakhlamova, L. in C.A. 89:110440p and 85:62609u.

However, fluoroalkyl compounds which are terminally branched or contain omega-hydrogen atoms do not exhibit efficient oil repellency. Perfluoroalkyl compounds which are connected directly via hetero-atoms without alkylene spacers are not sufficiently flexible as pendant groups. Perfluoroalkylmethylene-hetero groups, other than trifluoroethylene, are expensive to prepare. Consequently, such fluoroalkyl oxetanes are not practical intermediates from which to obtain useful products. Additionally, other perfluoroalkyl compounds containing heteroaromatic connecting groups or mono-fluoroalkyl oxetanes containing oxygen have been reported e.g. J. Org. Chem. 45 (19) 3930 (1980). These compounds are not useful for purposes of this invention.

The subject perfluoroalkyl oxetanes are readily isolated in high yield and purity. Since the subject oxetanes are connected to the linear, pendant perfluoroalkyl chains by flexible hetero groups, more mobile perfluoroalkyl functions are provided, which exhibit optimal oil repellency.

Bis-perfluoroalkyl oxetanes, polymeric derivatives thereof, and their reaction products with nucleophiles are useful because they possess a low free surface energy which provides oil and water repellency to a wide variety of substrates. Oxetanes containing a single $R_f$-function, multiple $R_f$-functions with terminal hydrogen atoms, or branched perfluoroalkyl groups are known, but do not provide these properties to the same extent. The subject oxetanes may be prepared in high yield and purity in contrast to prior art materials.

DETAILED DISCLOSURE

This invention relates to a method of making 3,3-bis-perfluoroalkyl substituted $R_f$-oxetanes and their derived polyethers. In one embodiment, the polymers are homopolymers. In another they are block polymers and contain 1-90% of a fluorochemical block connected to 99-10% by weight of a non-fluorochemical block. This invention also relates to the reaction products of said oxetanes with nucleophiles to form neopentyl alcohols. Other aspects of this invention are the substitution of the alcohol function by halide and the derivatization of the alcohols as esters or urethanes. The compositions are useful per se or intermediates for coatings on textiles, glass, linoleum, leather, wood, tile, metals, plastics and other various materials.

This invention most generally relates to novel heteroatom containing perfluoroalkyl terminated neopentyl oxetanes and derived polymers containing residues from said $R_f$-oxetanes.

Another aspect of this invention relates to a substrate containing 0.01 to 10% by weight of a fluorine-containing polyether composition, at least part of said fluorine being provided by one or more units derived from the heteroatom containing $R_f$-neopentyl oxetane, to become oil and water repellent.

The novel heteroatom containing $R_f$-neopentyl oxetanes have the general formula I or II

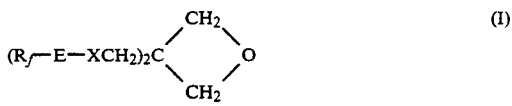

or

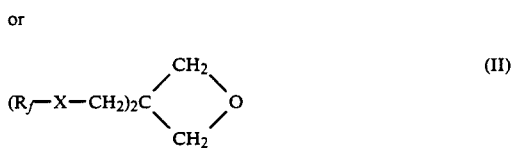

wherein $R_f$ is a straight chain perfluoroalkyl of 1 to 18 carbon atoms, E is branched or straight chain alkylene of 2 to 10 carbon atoms, or said alkylene interrupted by one to three groups selected from the group consisting of —NR—, —O—, —S—, $SO_2$—, —COO—, —OOC—, —CONR—, —NRCO—, —$SO_2$NR—, and —NR$SO_2$—, or terminated at the $R_f$ end with —CONR— or —$SO_2$NR—, where $R_f$ is attached to the carbon or sulfur atom, or $R_f$—E is trifluoroethylene, i.e. $CF_3CH_2$ and for formula I, X is —S—, —O—, —$SO_2$—, or —NR—, or for formula II, X is —CONR—, —$SO_2$NR—, or a direct bond where $R_f$ is attached to the carbon or sulfur atom, and where R is independently hydrogen, alkyl of 1 to 6 carbon atoms or hydroxyalkyl of 2 to 6 carbon atoms.

Further, the 3,3-substituents need not be identical, though identical groups are preferred.

Novel polymers are derived from the aforementioned oxetanes.

It is understood that the $R_f$ group usually represents a mixture of linear perfluoroalkyl moieties. When the $R_f$ group is identified as having a certain number of carbon atoms, the said $R_f$ group also usually concomitantly contains a small fraction of perfluoroalkyl groups with a lower number of carbon atoms and a small fraction of perfluoroalkyl groups with a higher number of carbon atoms.

Preferably the instant compounds of formula I are those where $R_f$ is perfluoroalkyl of 2 to 12 carbon atoms, E is alkylene of 2 to 6 carbon atoms, —CONHCH$_2$CH$_2$—, —CH$_2$CH$_2$N(CH$_3$)CH$_2$CH$_2$—, —CH$_2$CH$_2$SO$_2$NHCH$_2$CH$_2$—, —CH$_2$CH$_2$OCH$_2$CH$_2$—, or —SO$_2$NHCH$_2$CH$_2$—, and X is —S—, —SO$_2$— or —O—. A preferred embodiment is where $R_f$ is a mixture of $C_4F_9$, $C_6F_{13}$, $C_8F_{17}$ and $C_{10}F_{21}$.

Most preferred are those compounds of formula I where $R_f$ is perfluoroalkyl of 6 to 12 carbon atoms, E is ethylene, and X is S, i.e.,

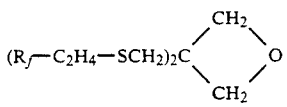

In another group of most preferred compounds $R_f$ is perfluoroalkyl of 6 to 12 carbon atoms, E is ethylene, and X is O, i.e.,

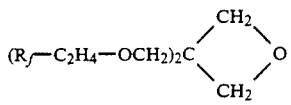

The novel $R_f$-oxetanes can be obtained directly by the reaction of a perfluoroalkyl thiol of formula $R_f$—E—SH, perfluoroalkyl amine of formula $R_f$—E—NR$_2$, perfluoroalkanol of formula $R_f$—E—OH, or a perfluoroalkyl-sulfonamide of formula $R_f$—SO$_2$NHR with a bis-haloalkyl oxetane of formula

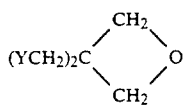

where Y is Cl, Br, or I.

In one preferred embodiment, the starting material is bis-bromomethyl oxetane and has the formula

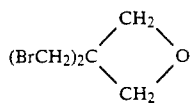

This intermediate is commercially available in high purity. Dichloro and diiodo neopentyl oxetanes have also been reported.

The synthesis of $R_f$-oxetanes proceeds by the nucleophilic substitution of a perfluoroalkyl substituted thiol, alcohol, sulfonamide amine for halide. The reaction is preferably conducted in an aqueous system using phase transfer catalysis for the thiolate and amine. An alternate process, in anhydrous media, is best for the alcohol and involves the combination of:

a. an aprotic solvent, such as N-methylpyrrolidone, N,N-dimethylformamide, dimethyl sulfoxide, or the like, or ketones, such as acetone, methyl alkyl ketones, or dialkyl ketones.

b. moderate reaction temperature, on the order of 50° to about 120° C.; and c. a stoichiometric quantity of an anhydrous alkaline earth carbonate, preferably potassium carbonate, in the ratio of 1 mole of carbonate per mole of halide to be displaced.

With certain amines, tertiary amine catalysis is useful, as exemplified by triethylamine, tributylamine, dimethylaminopyridine, or piperidine. With alcohols or sulfonamides, Crown ether catalysis is useful as exemplified by 12-Crown-4, 15-Crown-5, and 18-Crown-6.

The reaction temperature and choice of solvent are mutually dependent. A reaction temperature in the range of 50°-140° C. is one wherein the formation of undesirable by-products is minimized and the reaction products are stable. Conditions are adjusted in order to achieve a reasonable rate of reaction at the chosen temperature.

In the synthesis of the $R_f$-oxetanes, by-products may be present. When the starting thiol is $R_f$CH$_2$CH$_2$SH and bis-bromomethyl oxetane is used, the by-products include

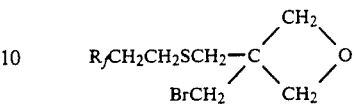

Such an intermediate is consistent with the general reaction conditions. It should be noted that the ready oxidation of thiols to disulfides requires that the chemistry be conducted in an inert atmosphere.

The subject oxetanes can also be made by first reacting the bromo-oxetane intermediates with a functional thiol or amine, i.e. HSCH$_2$CH=CH$_2$, HSCH$_2$COOH or NH$_2$CH$_2$CH=CH$_2$. The resultant sulfide or amine can then be reacted with the $R_f$-containing moiety by a suitable chemistry which does not involve the pendant oxetane. The reactant may be $R_f$I, $R_f$CH$_2$CH$_2$I, $R_f$CH$_2$CH$_2$OH or a like monofunctional $R_f$-reactant. If iodine atoms are introduced they may be removed by reduction, dehydrohalogenation, or coupling.

For example,

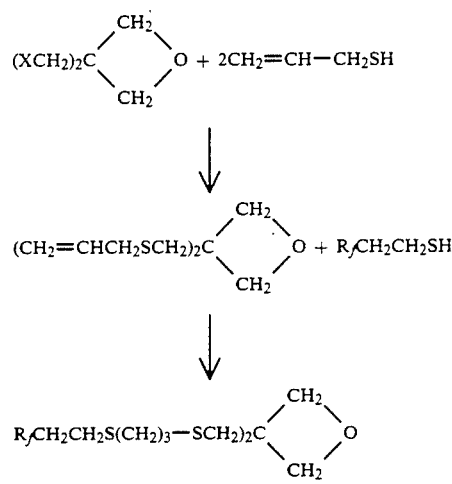

The subject sulfido-oxetanes can be readily oxidized to the corresponding bis-sulfone oxetanes by peracetic acid (H$_2$O$_2$/acetic acid) or by other conventional oxidants. With peracetic acid, temperatures of 30°-100° C. are appropriate depending on the amount of excess oxidizing agent to ensure that the intermediate sulfoxides are completely oxidized.

Perfluoroalkyl thiols useful herein are well documented in the prior art. For example, thiols of the formula $R_f$—E—SH have been described in a number of U.S. Pat. Nos. including 3,655,732 and 4,584,143.

Thus, U.S. Pat. No. 3,655,732 discloses mercaptans of formula $R_f$—E—SH where

E is alkylene of 1 to 16 carbon atoms and $R_f$ is perfluoroalkyl, and teaches that halides of formula $R_f$—E—Halide are well-known; reaction of $R_f$I with ethylene under free-radical conditions gives $R_f$(CH$_2$CH$_2$)I while reaction of $R_f$CH$_2$I with ethylene gives $R_f$CH$_2$(CH$_2$CH$_2$)$_a$I as is further taught in U.S. Pat. Nos. 3,088,849; 3,145,222; 2,965,659 and 2,972,638.

U.S. Pat. No. 3,655,732 further discloses compounds of formula R$_f$—R'—Y—R''—SH where R' and R'' are alkylene of 1 to 16 carbon atoms, with the sum of the carbon atoms of R' and R'' being no greater than 25; R$_f$ is perfluoroalkyl of 4 through 14 carbon atoms and Y is —S— or —NR'''— where R''' is hydrogen or alkyl of 1 through 4 carbon atoms.

U.S. Pat. No. 3,544,663 teaches that the mercaptan R$_f$CH$_2$CH$_2$SH where R$_f$ is perfluoroalkyl of 5 to 13 carbon atoms, can be prepared by reacting the perfluoroalkyl alkylene iodide with thiourea or by adding H$_2$S to a perfluoroalkyl substituted ethylene (R$_f$—CH=CH$_2$), which in turn can be prepared by dehydrohalogenation of the R$_f$—CH$_2$CH$_2$— halide.

The reaction of the iodide R$_f$—E—I with thiourea followed by hydrolysis to obtain the mercaptan R$_f$—E—SH is the preferred synthetic route. The reaction is applicable to both linear and branched chain iodides.

Particularly preferred herein are the thiols of formula

R$_f$CH$_2$CH$_2$SH where

R$_f$ is perfluoroalkyl of 6 to 12 carbon atoms. These R$_f$-thiols can be prepared from R$_f$CH$_2$CH$_2$I and thiourea in very high yield.

Perfluoroalkylamines useful herein are well documented in the prior art. For example, C$_6$F$_{13}$CH$_2$CH$_2$NH$_2$ has been described in Japan Kokai 77/118,406. R$_f$CH$_2$NH$_2$ wherein R$_f$ is CF$_3$ through CF$_3$(CF$_2$)$_{11}$ are described in British Patent No. 717,232 (1954).

Further R$_f$SO$_2$NR(CH$_2$)$_m$NR(CH$_2$)$_3$NH$_2$ and R$_f$CH$_2$CH$_2$SO$_2$NH(CH$_2$)$_m$NR$_2$ are described in G.B. 1,106,641 and U.S. Pat. No. 3,838,165 respectively; R$_f$CONH(CH$_2$)$_m$NH$_2$ in Jap. Kokai 52/14767.

Perfluoroalkanols useful herein are well documented in the prior art, and many are commercially available. They have the general formula R$_f$—E—OH and include the following:

C$_8$F$_{17}$SO$_2$N(C$_2$H$_5$)C$_2$H$_4$OH

C$_8$F$_{17}$C$_2$H$_4$OH

C$_7$F$_{15}$CON(C$_2$H$_5$)C$_2$H$_4$OH

C$_8$F$_{17}$C$_2$H$_4$SC$_2$H$_4$OH

C$_8$F$_{17}$C$_2$H$_4$SO$_2$N(CH$_3$)C$_4$H$_8$OH

C$_8$F$_{17}$CH$_2$CH$_2$SO$_2$NHCH$_2$CH$_2$OH.

Perfluoroalkylsulfonamides useful herein are well documented in the prior art such as in U.S. Pat. No. 2,915,554 and include compounds of the general structure R$_f$—SO$_2$NHR, such as

C$_8$H$_{17}$SO$_2$N(C$_2$H$_5$)OH

C$_8$F$_{17}$SO$_2$N(CH$_3$)H

C$_8$F$_{17}$SO$_2$N(i-C$_3$H$_7$)H

C$_{10}$F$_{21}$SO$_2$N(C$_2$H$_5$)H

C$_{10}$F$_{21}$SO$_2$NH$_2$

The oxetanes can be used directly or indirectly by reaction with nucleophiles to make a variety of products. Such nucleophiles as halide ions, thiourea, alcohols and thiols can be used as described in Heterocyclic Compounds by Weissberger, Vol 19 (II), under Oxetanes by S. Searles, Jr.

The instant invention also related to novel heteroatom containing R$_f$-neopentyl compounds having the formula III or IV

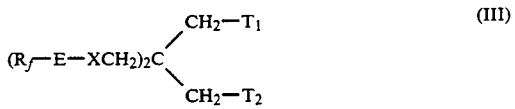

or

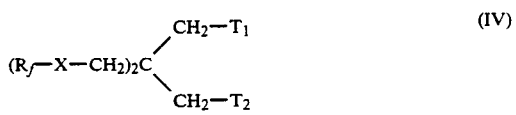

wherein R$_f$ is a straight chain perfluoroalkyl of 1 to 18 carbon atoms, E is branched or straight chain alkylene of 2 to 10 carbon atoms, or said alkylene interrupted by one to three groups selected from the group consisting of —NR—, —O—, —S—, SO$_2$—, —COO—, —OOC—, —CONR—, —NRCO—, —SO$_2$NR—, and —NRSO$_2$—, or terminated at the R$_f$ end with —CONR— or —SO$_2$NR—, where R$_f$ is attached to the carbon or sulfur atom, R$_f$—E is trifluoroethylene, and for formula III, X is —S—, —O—, —SO$_2$—, or —NR—, or for formula IV, X is —CONR—, —SO$_2$NR—, or a direct bond where R$_f$ is attached to the carbon or sulfur atom, and where R is independently hydrogen, alkyl of 1 to 6 carbon atoms or hydroxyalkyl of 2 to 6 carbon atoms, and T$_1$ and T$_2$ are independently chloro, bromo, or iodo, or where one of T$_1$ and T$_2$ is hydroxyl, alkanoyloxy of 2 to 18 carbon atoms, alkenoyloxy of 2 to 18 carbon atoms or benzoyloxy, and the other of T$_1$ and T$_2$ is defined above; or where one or both of T$_1$ and T$_2$ is the residue of a mercapto mono- or di-carboxylic acid of 2 to 4 carbon atoms after removal of the hydrogen atom from the mercapto group, and the other of T$_1$ and T$_2$ is hydroxyl. Preferably the mercapto acid is mercaptoacetic, thiolactic, 3-mercaptopropionic or thiosuccinic acid.

When one of T$_1$ and T$_2$ is alkanoyloxy, said group is for example acetoxy, propionyloxy, butyryloxy, caproyloxy, capryloyloxy, nonanoyloxy, lauroyloxy or octadecanoyloxy.

When one of T$_1$ and T$_2$ is alkenoyloxy, said group is for example acryloyloxy, methacryloyloxy or oleoyloxy.

Preferably one of T$_1$ and T$_2$ is hydroxyl and the other of T$_1$ and T$_2$ is chloro, bromo, or iodo.

In another preferred embodiment, both of T$_1$ and T$_2$ are chloro, bromo or iodo, most preferably bromo.

It is understood that the R$_f$ group usually represents a mixture of linear perfluoroalkyl moieties. When the R$_f$ group is identified as having a certain number of carbon atoms, the said R$_f$ group also usually concomitantly contains a small fraction of perfluoroalkyl groups with a lower number of carbon atoms and a small fraction of perfluoroalkyl groups with a higher number of carbon atoms.

Preferably the instant compounds of formula III are those where R$_f$ is perfluoroalkyl of 2 to 12 carbon atoms, E is alkylene of 2 to 6 carbon atoms, —CONHCH$_2$CH$_2$—, —CH$_2$CH$_2$N(CH$_3$)CH$_2$CH$_2$—, —CH$_2$CH$_2$SO$_2$NHCH$_2$CH$_2$—, —CH$_2$CH$_2$OCH$_2$CH$_2$—, or —SO$_2$NHCH$_2$CH$_2$—, and X is —S—, —SO$_2$— or —O—. A preferred embodiment is where R$_f$ is a mixture of C$_4$F$_9$, C$_6$F$_{13}$, C$_8$F$_{17}$ and C$_{10}$F$_{21}$.

Most preferred are those compounds of formula III where R$_f$ is perfluoroalkyl of 6 to 12 carbon atoms, E is ethylene, and X is S.

In another group of most preferred compounds R$_f$ is perfluoroalkyl of 6 to 12 carbon atoms, E is ethylene, and X is O.

Polyethers derived from non-fluorinated oxetanes are well known and are also described by Searles in the previous citation. The derived polyethers are generally prepared from the corresponding oxetane monomer by cationic polymerization, most typically with a powerful electrophile such as boron trifluoride or its etherate. Polymerization occurs rapidly and exothermically and is generally conducted in solution. A co-catalyst of water appears necessary and high molecular weight polymers can be obtained. The polymer of 3,3-bis(chloromethyl) oxetane was known commercially as "Penton" and has good electrical molding, dimensional stability and solubility properties. It is no longer manufactured.

Numerous 3,3-disubstituted oxetanes have been reported, including several highly branched perfluoroalkyl derivatives, and several have been polymerized.

Polyethers derived from the instant linear 3,3-bis-perfluoroalkyl oxetanes can also be copolymerized with tetrahydrofuran and block copolymers prepared by the method taught by S. V. Conjeevaram, et. al. in J. Polymer Sci., 23, 429–444 (1985).

These polyethers have extremely low free surface energies and therefore, possess oil and water repellent properties, as well as mold release and other properties associated with low free surface energy. It should be noted that the compositions of this invention are characterized by the presence of two perfluoroalkylhetero groups in close proximity, a characteristic which provides improved oil and water repellent properties over the fluorinated compositions of the prior art.

Furthermore the two perfluoroalkylthio groups are connected via a neopentyl moiety which does not permit the thermal elimination of mercaptan by beta-elimination. Hence, these R$_f$-oxetanes and their derivatives with various nucleophilic species have enhanced thermal stability. It should be noted that the reaction of oxetanes and HCl, HBr, or HI yields halohydrins.

The alcohol function of these halohydrins can be halogenated to form dihalo compounds. Other chemistries normally exhibited by alcohols can be accomplished, such as esterification, etc.

The halohydrins or dihalo derivatives can also be reacted with mercapto-acids to yield bis-perfluoroalkyl carboxylates useful as paper sizes.

Using the R$_f$-compounds and polyethers described herein, it is possible to manufacture molds that display excellent release properties. It is also possible to prepare polymeric compositions with enhanced thermal stability.

Treatment of a textile with a fluorine-containing composition, notably a bis-perfluoroalkyl containing polymer, provides outstanding oil and water-repellent characteristics thereto.

The invention described above is illustrated by the following examples:

Examples 1 to 6 illustrate the preparation of the R$_f$-oxetanes.

Examples 7 to 11 demonstrate the wide diversity of nucleophilic reaction products and related compounds that can readily be prepared from the subject oxetanes.

Example 12 demonstrates the formation of a polyether derived from an oxetane and its excellent oil/water repellency.

Examples 14–20 show the preparation of additional R$_f$-substituted oxetanes.

EXAMPLE 1

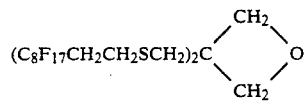

3,3-Bis(1,1,2,2-tetrahydroperfluorodecylthiomethyl)oxetane 3,3-Bis(bromomethyl)oxetane (15.0 g, 0.061 mol) is charged to a three neck-flask with 1,1,2,2-tetrahydroperfluorodecyl mercaptan (62.3 g, 0.13 mol). Toluene (90.0 g), distilled water (60.0 g) and sodium hydroxide (20.0 g, 50%) are added and the mixture is stirred under nitrogen. Tricaprylylmethylammonium chloride, a phase transfer catalyst, (0.5 g) is then added with stirring and the reaction mixture is heated to 95° C. under reflux for 2.5 hours. The toluene layer containing the product is separated hot from the lower alkaline layer by a separatory funnel and cooled to precipitate the product. The product is filtered, washed three times with cold toluene and dried under vacuum to yield an off-white solid, mp 82°–83° C., 97% purity by GLC. NMR shows proton resonances at 2.42 ppm, 4 protons, (2×CH$_2$CH$_2$S); 2.82 ppm, 4 protons, (2×CH$_2$CH$_2$S); 3.09 ppm, 4 protons, (2×CH$_2$CH$_2$SCH$_2$); 4.56 ppm, 4 protons, (CH$_2$OCH$_2$).

Analysis for C$_{25}$H$_{16}$F$_{34}$S$_2$O; Calculated: C, 28.8%; H, 1.5%, F, 62.0%; S, 6.2%. Found: C, 28.6%; H, 1.3%, F, 61.7%; S, 6.6%.

EXAMPLE 2

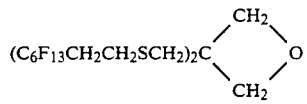

3,3-Bis(1,1,2,2-tetrahydroperfluoro-octylthiomethyl)oxetane 3,3-Bis(bromomethyl)oxetane (15.0 g, 0.06 mol) is charged to a three-neck flask with 1,1,2,2-tetrahydroperfluoro-octyl mercaptan (51.08 g, 0.134 mol). Toluene (90.0 g), distilled water (60.0 g) and sodium hydroxide (20.0 g, 50%) are added, and the mixture is stirred under nitrogen. Tricaprylylmethylammonium chloride, a phase transfer catalyst 0.5 g), is then added with stirring, and the reaction mixture is heated to 95° C. under reflux for 1.5 hours. The toluene layer containing the product is separated from the lower alkaline layer and then cooled to precipitate the product. The product is filtered cold, washed three times with cold toluene and dried under vacuum to yield an off-white solid, mp 45.5°–46° C., 99.5% purity by GLC. NMR shows proton resonances at 2.42 ppm, 4 protons, (2×CH₂CH₂S); 2.82 ppm, 4 protons, (2×CH₂CH₂S); 3.09 ppm, 4 protons, (2×CH₂CH₂SCH₂); 4.45 ppm, 4 protons, (CH₂OCH₂).

Analysis for $C_{21}H_{16}F_{26}S_2O$: Calculated: C, 30.0%; H, 1.9%, F, 58.6%; S, 7.6%. Found: C, 29.8%; H, 1.8%, F, 58.6%; S, 8.2%.

EXAMPLE 3

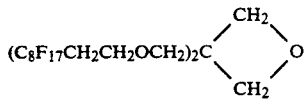

3,3-Bis(1,1,2,2-tetrahydroperfluorodecyloxymethyl)oxetane 1,1,2,2-Tetrahydroperfluoro-octanol (10.9 g, 0.03 mol), 3,3-(bromomethyl)oxetane (3.9 g, 0.016 mol), potassium hydroxide (1.7 g, 0.03 mol) and 15 g of diethylene glycol dimethyl ether are reacted in the presence of approximately 1.0 g of 18 Crown-6 in a 50 ml flask with gentle stirring for 72 hours at room temperature. Analysis by gas chromatography indicates that the solution contains 36% monoadduct and 64% diadduct. 2.5 g of solids are filtered off and GC/MS identification confirms the presence of the desired 3,3-(1,1,2,2-tetrahydroperfluoro-octyloxy)oxetane and 3-(1,1,2,2-tetrahydroperfluoro-octyloxy)-3-bromo-oxetane.

Identification is made by GC/MS (E.I. Mode) after derivatization with N,O-bis-(trimethylsilyl)-trifluoroacetamide. Two major components are observed:

(Diadduct): MS: m/z 810 absent, 780 (M—CH₂O), 417 b.p., (M—C₆F₁₃CH₂CH₂O), 403 (M—C₆F₁₃CH₂C-H₂OCH₊₂). MS (CI) 811 (M+1)+.

(Monoadduct): MS: m/z 526 absent, 447 (M—Br), 417 b.p.(M—CH₂OBr). MS (CI) 527 (M+1)+.

EXAMPLE 4

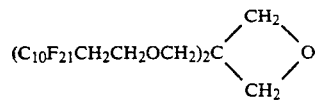

3,3-Bis(1,1,2,2-tetrahydroperfluorododecyloxymethyl)oxetane

In a similar fashion to Example 3, 1,1,2,2-tetrahydroperfluorododecanol is reacted at 100° C. for 2-3 hours to give a mixture of monoadduct-40% and diadduct-60%.

EXAMPLE 5

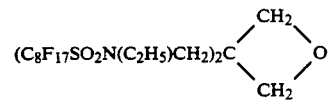

3,3-Bis(N-ethylperfluoro-octanesulfonamidomethyl)oxetane

A mixture of N-ethylperfluoro-octanesulfonamide (20.0 g, 0.047 mol), 87% potassium hydroxide (3.0 g, 0.047 mol), diethylene glycol dimethyl ether (60.0 g) and 18-Crown-6 ether (0.1 g) is heated under nitrogen at 100°-105° C. for 30 minutes. The 3,3-bis-(bromomethyl)-oxetane (5.7 g, 0.0236 mol) is then added, and the entire reaction mass is heated at 100° C. for 13 hours. The salts are removed by filtration, and the solvent is removed at 80° C. under vacuum. NMR shows the presence of the expected product.

EXAMPLE 6

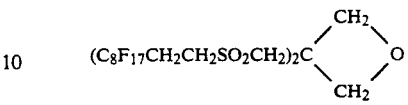

3,3-Bis(1,1,2,2-tetrahydroperfluorodecylsulfonylmethyl)oxetane 3,3-Bis(1,1,2,2-tetrahydroperfluorodecylthiomethyl)oxetane (15.0 g, 0.014 mol) is dissolved in glacial acetic acid (44.27 g, 0.737 mol) and warmed to 40° C. Hydrogen peroxide (4.0 g, 30%) is added, and the mixture is stirred for 1 hour. The reaction mixture is then heated to 100° C., and additional hydrogen peroxide (11.0 g, 30%) is added. The mixture is stirred for 2.5 hours under reflux. The product, a white precipitate, is filtered, washed with ethanol and dried under vacuum, (13.85 g, 90% of theory) 93% purity by GLC. The product is recrystallized from isopropyl acetate two times and dried under vacuum to yield a white solid (8.59 g, 56% of theory), mp 162°-4° C., 98% purity by GLC. NMR shows proton resonances at 2.90 ppm, complex, 4 protons, (2×C₈F₁₇CH₂); 3.65 ppm triplet, 4 protons, (2×C₈F₁₇CH₂CH₂); 4.25 ppm, singlet, 4 protons, (2×CH₂SO₂CH₂); 4.80 ppm, singlet, 4 protons, (oxetane ring).

Analysis for $C_{25}H_{16}F_{34}O_5S_2$: Calculated: C, 27.1%; H, 1.5%; F, 58.4%; S, 5.8%. Found: C, 26.8%; H, 1.4%; F, 58.4%; S, 5.5%.

EXAMPLE 7

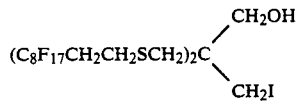

2,2-Bis(1,1,2,2-tetrahydroperfluorodecylthiomethyl)-3-iodo-1-propanol 3,3-Bis(1,1,2,2-tetrahydroperfluorodecylthiomethyl)oxetane (2.0 g, 0.010 mol) is dissolved in tert-butyl alcohol (4.0 g, 0.054 mol). Hydriodic acid (1.0 g, 57%, 0.0045 mol) is added to the mixture, which is then heated to 60° C. for 10 minutes. The product is precipitated from H₂O and then vacuum filtered. The product (1.65 g, 71% of theory) is a yellow solid, 92% purity by GLC. For analytical purposes, the crude product is crystallized from heptane, which yields a white solid (1.30 g, 56% of theory), mp 58°-60° C., 98% purity by GLC. NMR shows proton resonances at 2.43 ppm, complex, 4 protons, (2×C₈F₁₇CH₂); 2.72 ppm, singlet, 4 protons (2×SCH₂); 2.85 ppm, triplet, 4 protons, (2×CHX₂S); 3.55 ppm, singlet, 2 protons, (CH₂I); 3.66 ppm, singlet, 2 protons, (CH₂OH). OH is not observed.

Analysis for $C_{25}H_{17}F_{34}IOS_2$: Calculated: C, 25.7%; H, 1.5%; F, 55.2%. Found: C, 25.4%; H, 1.4%; F, 54.8%.

EXAMPLE 8

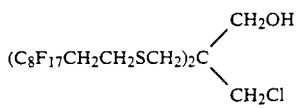

2,2-Bis(1,1,2,2-tetrahydroperfluorodecylthiomethyl)-3-chloro-1-propanol 3,3-Bis(1,1,2,2-tetrahydroperfluorodecylthiomethyl)oxetane (1.0 g, 0.001 mol) is dissolved in tert-butyl alcohol (2.0 g, 0.054 mol). Hydrochloric acid (1.2 g, 37.7%, 0.011 mol) is added to the mixture, which is then heated to 60° C. for 10 minutes. The product is precipitated from $H_2O$ (15 g), vacuum filtered and dried in a desiccator over drierite. This procedure yields an off-white solid (0.40 g, 37% of theory), mp 60°-1° C., 96% purity by GLC. NMR shows proton resonances at 2.4 ppm, complex, 4 protons, $(2 \times C_8F_{17}CH_2)$; 2.7 ppm, singlet, 4 protons, $(2 \times CH_2S)$; 2.85 ppm, triplet, 4 protons, $(2 \times SCH_2)$; 3.65 ppm, singlet, 4 protons, $(CH_2Cl$ and $CH_2OH)$. OH is not observed.

Analysis for $C_{25}H_{17}ClF_{34}OS_2$: Calculated: C, 27.8%; H, 1.6%; F, 59.9%. Found: C, 27.6%; H, 1.3%; F, 59.5%.

EXAMPLE 9

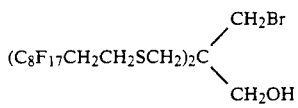

2,2-Bis(1,1,2,2-tetrahydroperfluorodecylthiomethyl)-3-bromo-1-propanol 2,2-Bis(1,1,2,2-tetrahydroperfluorodecylthiomethyl)oxetane (7.0 g, 0.0067 mol) is charged to a three-neck flask with hydrobromic acid (48%, 2.5 g, 0.0015 mol) and toluene (20.0 g). The reaction is heated at 100° C. under nitrogen with stirring for 2 hours. The water/toluene azeotrope is then removed to 110° C. The toluene concentrate is then cooled and the product precipitates. The product is filtered, washed three times with cold toluene and dried under vacuum to yield a white solid, mp 63°-64° C., 98% purity by GLC. NMR shows proton resonances at 1.70 ppm, 1 proton, (—OH); 2.25-2.60 ppm, 4 protons, $(2 \times R_fCH_2)$; 2.7-2.9 ppm, 8 protons, $(2 \times CH_2$—S—$CH_2)$; 3.53 ppm, 2 protons, $(CH_2Br)$; 3.67 ppm, 2 protons, $(CH_2OH)$.

Analysis for $C_{25}H_{17}F_{34}BrOS_2$: Calculated: C, 26.7%; H, 1.5%; Br, 7.1%; F, 57.5%; S, 5.7%. Found: C, 26.4%; H, 1.4%; Br, 7.3%; F, 55.9%; S, 6.1%.

EXAMPLE 10

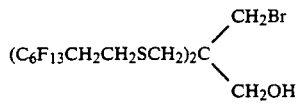

2,2-Bis(1,1,2,2-tetrahydroperfluorooctylthiomethyl)-3-bromo-1-propanol 3,3-Bis(1,1,2,2-tetrahydroperfluoro-octylthiomethyl)oxetane (7.0 g, 0.0083 mol) is charged to a three-neck flask with hydrobromic acid (48%, 3.1 g 0.018 mol) and toluene (20.0 g). The reaction is heated at 100° C. under nitrogen with stirring for 4 hours. The water/toluene azeotrope is then removed at 110° C. The solvent is then removed under vacuum to yield a thick brown liquid which is 99% pure by GLC. NMR shows proton resonances at 1.80 ppm, 1 proton, (—OH), 2.2-2.6 ppm, 4 protons, $(2 \times R_fCH_2)$; 2.7-2.9 ppm, 8 protons, $(2 \times CH_2SCH_2)$; 3.53 ppm, 2 protons, $(CH_2Br)$; 3.65 ppm, 2 protons, $(CH_2OH)$.

Analysis for $C_{21}H_{17}OS_2F_{26}Br$: Calculated: C, 27.3%; H, 1.9%, Br, 8.7%; F, 53.5%, S, 7.0%. Found: C, 27.1%; H, 1.7%; Br, 9.1%; F, 51.5%; S, 7.1%.

EXAMPLE 11

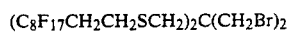

2,2-Bis(1,1,2,2-tetrahydroperfluorodecylthiomethyl)1,3-dibromopropane 2,2-Bis(1,1,2,2-tetrahydroperfluorodecylthiomethyl)-3-bromopropanol (10.0 g, 9 mmol) is charged to a three necked flask with phosphorus tribromide (4.3 g, 16 mmol). The reaction mixture is heated at 100° C. under nitrogen for 2 hours to give the desired product which is recrystallized from toluene.

Identification is made by GC/MS (EI mole).

MS: m/z 1184 (m+) 1165 (m-f), 739 (b.p.), 493.

EXAMPLE 12

Poly-[2,2-Bis(1,1,2,2-tetrahydroperfluorodecylthiomethyl)-trimethylene ether]

3,3-Bis(1,1,2,2-tetrahydroperfluorodecylthiomethyl)oxetane (10.0 g, 0.0096 mol) is dissolved in trifluorotrichloroethane and boron trifluoride etherate (2.0 ml) is added as catalyst. The reaction mixture is stirred at room temperature for 0.5 hr. The product, a white precipitate, is then vacuum filtered, washed two times with trifluorotrichloroethane and dried under high vacuum, yielding a white solid (8.44 g). Several analyses confirm the presence of the desired polymer.

Analysis: for $(C_{25}H_{16}F_{34}S_2O)_n$: Calculated: C, 28.8%; H, 1.5%; S, 6.1%. Found: C, 26.6%; H, 1.5%; S, 6.0%.

The $^1H$ NMR spectra obtained by silylation experiments indicates a repeat unit n, of 9-10.

DSC scans of the polymer were run at 10° C./min. to 350° C., 100 ml $N_2$/min. in open aluminum pans with a DuPont 990 Thermal Analyzer and a DSC cell base. The scans indicate an endothermic melting transition ($T_x$ (extrapolated onset temperature)=116° C., $T_{peak}$=121° C.), irreversible decomposition transitions ($T_{peak}$=140° C. and 164° C.) and a major irreversible decomposition transition ($T_{peak}$=243° C.).

TGA scans were run at 10° C./min. to 550° C., 100 ml $N_2$/min. using a DuPont 951 TGA module. The scans show a 22% weight loss from 150°-305° C. and a second weight loss of 73% from 305°-450° C. A 1% residue remains at 450° C. (A 4% weight loss before T=150° C. is attributed to solvent loss.)

Using the Zisman technique, the critical surface tension of the polymer $\gamma_c$ is found to be 9.8 dyne/cm. This indicates that the polymer is oil and water repellent.

When a solution of said polyether in hexafluoroxylene is used to treat a textile surface to deposit 0.1% by weight thereon, the textile surfaces becomes oil and water repellant.

EXAMPLES 13 TO 19

Using the methods described and by techniques similar to Examples 1-6, the following additional perfluoroalkyl substituted oxetanes are prepared.

| Ex. | Thiol | Perfluoroalkyl Terminated Neopentyl Oxetane |
|---|---|---|
| 13 | $CF_3CF_2CH_2SH$ | $(CF_3CF_2CH_2SCH_2)_2C(CH_2)_2O$ (oxetane) |
| 14 | $C_6F_{13}(CH_2)_4SH$ | $(C_6F_{13}(CH_2)_4SO_2CH_2)_2C(CH_2)_2O$ |
| 15 | $C_8F_{17}CH_2CH_2CH_2SH$ | $(C_8F_{17}CH_2CH_2CH_2SCH_2)_2C(CH_2)_2O$ |
| 16 | $C_8F_{17}CH_2CH_2N(CH_3)CH_2CH_2CH_2SH$ | $(C_8F_{17}CH_2CH_2N(CH_3)CH_2CH_2CH_2SCH_2)_2C(CH_2)_2O$ |
| 17 | $C_8F_{17}SO_2NHCH_2CH_2OH$ | $(C_8F_{17}SO_2NHCH_2CH_2OCH_2)_2C(CH_2)_2O$ |
| 18 | $C_8F_{17}CH_2CH_2SO_2NHCH_2CH_2SH$ | $(C_8F_{17}CH_2CH_2SO_2NHCH_2CH_2SCH_2)_2C(CH_2)_2O$ |
| 19 | $C_7F_{15}CONHCH_2CH_2SH$ | $(C_7F_{15}CONHCH_2CH_2SCH_2)_2C(CH_2)_2O$ |

EXAMPLES 20-27

Using the methods described and by techniques similar to Examples 7-12, the following additional alcohols, dihalides, esters and polymers are prepared.

| Ex. | Product |
|---|---|
| 20 | $(CF_3CF_2CH_2SCH_2)_2C(CH_2OH)(CH_2Br)$ |
| 21 | $(C_8F_{17}SO_2NHCH_2CH_2SCH_2)_2C(CH_2OH)(CH_2I)$ |
| 22 | $(C_7F_{15}CONHCH_2CH_2SCH_2)_2C(CH_2Br)_2$ |
| 23 | $(C_8F_{17}CH_2CH_2SO_2NHC_2H_4SCH_2)_2C(CH_2Br)(CH_2Cl)$ |
| 24 | $(C_8F_{17}CH_2CH_2OCH_2)_2C(CH_2OH)(CH_2I)$ |
| 25 | $(C_6F_{13}CH_2CH_2SCH_2)_2C(CH_2O_2CCH_3)(CH_2Br)$ |
| 26 | $(C_{10}F_{21}CH_2CH_2SO_2CH_2)_2C(CH_2O_2C(CH_2)_7CH_3)(CH_2Br)$ |
| 27 | Poly[2,2-bis(1,1,2,2-tetrahydrotrifluoropropyloxymethyl)-trimethylene ether] |

EXAMPLE 28

$(C_8F_{17}CH_2CH_2SCH_2)_2C(CH_2OH)(CH_2-S-CH(CO_2H)CH_2CO_2H)$

2,2-Bis-(1,1,2,2-tetrahydroperfluorodecylthiomethyl)-3-(2,3-dicarboxy-1-thiapropyl)-1-propanol The bromohydrin of Example 9 (17.4 g, 16.6 mmol), diethyl thiosuccinate (6.5 g, 31 mmol), potassium carbonate (4.3 g, 31 mmol) and acetone (50 ml) is charged to a three-neck flask and heated at reflux overnight. Water is added and the mixture extracted three times with methyl propyl ketone. The product is purified by silica chromatography to yield a yellow oil which is 99% pure by GLC.

The above diethyl ester (9.5 g, 7.6 mmol) is dissolved in 20 ml of diglyme and water (3 ml) in a single neck flask. Sodium hydroxide (1.5 ml of a 50% aqueous solution) is added and the mixture allowed to stir overnight at room temperature. Water is added, and the mixture extracted with methyl propyl ketone. The aqueous layer was acidified and extracted with methyl propyl ketone. The solvent is removed under vacuum and the resultant yellow oil is precipitated into water to produce a white solid. NMR shows proton resonances at 2.5 ppm ($4 \times R_fCH_2$); 2.6-3.0 ppm ($10 \times SCH_2$; 3.51 ppm ($2 \times CH_2OH$); 3.72 ($1 \times SCHCO_2$).

Analysis for $C_{29}H_{22}F_{34}S_3O_5$: Calculated: C, 29.2%; H, 1.8%, F, 54.1%; S, 8.1%. Found: C, 28.9%, H, 1.7%; F, 53.9%, S. 8.2%.

EXAMPLE 29

2,2-Bis-(1,1,2,2-tetrahydroperfluorodecylthiomethyl)-1,3-bis-(2-carboxy-1-thiaethyl) propane $(C_8F_{17}CH_2CH_2SCH_2)_2C(CH_2SCH_2CO_2H)_2$ The dibromide from Example 11 (25 g, 21 mmol), ethyl 2-mercaptoacetate (5.1 g, 41 mmol), potassium carbonate (5.8 g, 42 mmol), and acetone (70 ml) is reacted and purified as described in Example 28.

The resultant diester is saponified, acidified and precipitated into water to yield a white powder.

What is claimed is:

1. A heteroatom containing $R_f$-neopentyl compound having formula III or IV

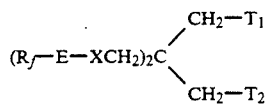
(III)

or

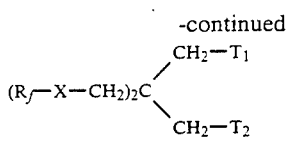
(IV)

wherein $R_f$ is a straight chain perfluoroalkyl of 1 to 18 carbon atoms, E is branched or straight chain alkylene of 2 to 10 carbon atoms or said alkylene interrupted by one to three groups selected from the group consisting of —NR—, —S—, SO$_2$—, —CONR—, —NRCO—, —SO$_2$NR—, and —NRSO$_2$—, or terminated at the $R_f$ end with —CONR— or —SO$_2$NR—, where $R_f$ is attached to the carbon or sulfur atom, or $R_f$—E is CF$_3$CH$_2$, and for formula III, X is —S—, —SO$_2$—, or —NR—, or for formula IV, X is —CONR—, or —SO$_2$NR—, or a direct bond where $R_f$ is attached to the carbon or sulfur atom, and where R is independently hydrogen, alkyl of 1 to 6 carbon atoms or hydroxyalkyl of 2 to 6 carbon atoms, and
one or both of $T_1$ and $T_2$ is the residue of a mercapto mono- or di-carboxylic acid of 2 to 4 carbon atoms after removal of the hydrogen from the mercapto group, and the other of $T_1$ and $T_2$ is hydroxyl.

2. A compound according to claim 1 wherein $R_f$ is a straight chain perfluoroalkyl of 2 to 12 carbon atoms.

3. A compound according to claim 1 wherein $R_f$ is a mixture of $C_4F_9$, $C_6F_{13}$, $C_8F_{17}$ and $C_{10}F_{21}$.

4. A compound of formula III according to claim 1 wherein $R_f$ is perfluoroalkyl of 2 to 12 carbon atoms, E is alkylene of 2 to 6 carbon atoms, —CONHCH$_2$CH$_2$—, —CH$_2$CH$_2$N(CH$_3$)CH$_2$CH$_2$—, —CH$_2$CH$_2$SO$_2$NHCH$_2$CH$_2$—, —CH$_2$CH$_2$OCH$_2$CH$_2$— or —SO$_2$NHCH$_2$CH$_2$—, and X is —S—, —SO$_2$— or —O—.

5. A compound of formula III according to claim 1 wherein $R_f$ is perfluoroalkyl of 6 to 12 carbon atoms, E is ethylene and X is —S—.

6. A compound of formula III according to claim 1 wherein $R_f$ is perfluoroalkyl of 6 to 12 carbon atoms, E is ethylene and X is —O—.

7. A compound according to claim 1 wherein one of $T_1$ and $T_2$ is hydroxyl, and the other of $T_1$ and $T_2$ is a residue of a mercapto mono- or di-carboxylic acid of 2 to 4 carbon atoms after removal of the hydrogen atom from the mercapto group.

8. A compound according to claim 1 wherein both of $T_1$ and $T_2$ are a residue of a mercapto mono- or di-carboxylic acid of 2 to 4 carbon atoms after removal of the hydrogen atom from the mercapto group.

9. The compound according to claim 1 which is 2,2-bis(1,1,2,2-tetrahydroperfluorodecylthiomethyl)-3-(2,3-dicarboxy-1-thiapropyl)-1-propanol.

10. The compound according to claim 1 which is 2,2-bis(1,1,2,2-tetrahydroperfluorodecylthiomethyl)-1,3-bis(2-carboxy-1-thiaethyl)propane.

* * * * *